US 9,814,881 B2

(12) United States Patent
Moffitt

(10) Patent No.: US 9,814,881 B2
(45) Date of Patent: Nov. 14, 2017

(54) SYSTEMS AND METHODS FOR PROVIDING THERAPY USING ELECTRICAL STIMULATION TO DISRUPT NEURONAL ACTIVITY

(71) Applicant: Boston Scientific Neuromodulation Corporation, Valencia, CA (US)

(72) Inventor: Michael A. Moffitt, Valencia, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 52 days.

(21) Appl. No.: 14/861,664

(22) Filed: Sep. 22, 2015

(65) Prior Publication Data
US 2016/0082257 A1 Mar. 24, 2016

Related U.S. Application Data

(60) Provisional application No. 62/053,589, filed on Sep. 22, 2014.

(51) Int. Cl.
*A61N 1/00* (2006.01)
*A61N 1/36* (2006.01)

(52) U.S. Cl.
CPC ..... *A61N 1/36071* (2013.01); *A61N 1/36135* (2013.01); *A61N 1/36139* (2013.01)

(58) Field of Classification Search
CPC ................. A61N 1/36071; A61N 1/36135
(Continued)

(56) References Cited

U.S. PATENT DOCUMENTS

| 4,813,418 A | 3/1989 | Harris |
| 6,067,474 A | 5/2000 | Schulman et al. |

(Continued)

FOREIGN PATENT DOCUMENTS

| DE | 10318071 A1 | 11/2004 |
| WO | 02/09808 A1 | 2/2002 |
| WO | 2009/055127 A1 | 4/2009 |

OTHER PUBLICATIONS

Larson, J. et al., "Reversal of LTP by theta frequency stimulation", Brain Research, Elsevier, Amsterdam, NL, vol. 600 No. 1, Jan. 8, 1993, pp. 97-102.

(Continued)

*Primary Examiner* — Nadia A Mahmood
(74) *Attorney, Agent, or Firm* — Lowe Graham Jones PLLC; Bruce E. Black

(57) ABSTRACT

An electrical stimulation system includes an implantable control module having a processor. The control module provides electrical stimulation signals to one or more leads coupled to the control module for stimulation of patient tissue to treat pain. A first electrode is disposed on the one or more leads in the patient's spinal cord and communicates with the processor to generate a first effective electric field suitable for stimulating patient tissue using the electrical stimulation signals provided from the control module. A second electrode is disposed on the one or more leads and communicates with the processor to generate a second effective electric field suitable for stimulating patient tissue using the electrical stimulation signals provided from the control module. The second effective electric field is time-delayed from the first effective electric field such that the second effective electric field is out of phase with the first effective electric field.

16 Claims, 9 Drawing Sheets

(58) Field of Classification Search
USPC .................................................. 607/46, 118
See application file for complete search history.

(56) References Cited

U.S. PATENT DOCUMENTS

| | | | |
|---|---|---|---|
| 6,181,969 B1 | 1/2001 | Gord | |
| 6,516,227 B1 | 2/2003 | Meadows et al. | |
| 6,609,029 B1 | 8/2003 | Mann et al. | |
| 6,609,032 B1 | 8/2003 | Woods et al. | |
| 6,741,892 B1* | 5/2004 | Meadows | A61N 1/3752 607/116 |
| 7,244,150 B1 | 7/2007 | Brase et al. | |
| 7,437,193 B2 | 10/2008 | Parramon et al. | |
| 7,450,997 B1 | 11/2008 | Pianca et al. | |
| 7,672,734 B2 | 3/2010 | Anderson et al. | |
| 7,761,165 B1 | 7/2010 | He et al. | |
| 7,783,359 B2 | 8/2010 | Meadows | |
| 7,792,590 B1 | 9/2010 | Pianca et al. | |
| 7,809,446 B2 | 10/2010 | Meadows | |
| 7,917,221 B2 | 3/2011 | Tass | |
| 7,949,395 B2 | 5/2011 | Kuzma | |
| 7,974,698 B2 | 7/2011 | Tass et al. | |
| 7,974,706 B2 | 7/2011 | Moffitt et al. | |
| 8,000,794 B2 | 8/2011 | Lozano | |
| 8,000,795 B2 | 8/2011 | Lozano | |
| 8,000,796 B2 | 8/2011 | Tass et al. | |
| 8,078,275 B2 | 12/2011 | Lozano | |
| 8,116,874 B2 | 2/2012 | Tass | |
| 8,175,710 B2 | 5/2012 | He | |
| 8,224,450 B2 | 7/2012 | Brase | |
| 8,271,094 B1 | 9/2012 | Moffitt et al. | |
| 8,280,514 B2 | 10/2012 | Lozano et al. | |
| 8,295,944 B2 | 10/2012 | Howard et al. | |
| 8,346,365 B2 | 1/2013 | Lozano | |
| 8,364,278 B2 | 1/2013 | Pianca et al. | |
| 8,380,304 B2 | 2/2013 | Lozano | |
| 8,391,985 B2 | 3/2013 | McDonald | |
| 8,463,378 B2 | 6/2013 | Tass | |
| 8,463,386 B2 | 6/2013 | Tass | |
| 8,538,547 B2 | 9/2013 | Tass et al. | |
| 8,565,883 B2 | 10/2013 | Lozano | |
| 8,612,006 B2 | 12/2013 | Lozano et al. | |
| 8,868,191 B2 | 10/2014 | Lozano | |
| 9,227,066 B2 | 1/2016 | Lozano | |
| 2003/0191506 A1 | 10/2003 | Shloznikov | |
| 2004/0210271 A1 | 10/2004 | Campen | |
| 2005/0075696 A1 | 4/2005 | Forsberg et al. | |
| 2005/0216071 A1* | 9/2005 | Devlin | A61B 5/0476 607/48 |
| 2006/0015153 A1 | 1/2006 | Gliner et al. | |
| 2006/0212090 A1 | 9/2006 | Lozano et al. | |
| 2007/0142874 A1 | 6/2007 | John | |
| 2007/0150036 A1 | 6/2007 | Anderson | |
| 2007/0225674 A1 | 9/2007 | Molnar et al. | |
| 2008/0071325 A1 | 3/2008 | Bradley | |
| 2008/0215113 A1 | 9/2008 | Pawlowicz | |
| 2009/0055127 A1* | 2/2009 | Tu | H03M 1/1019 702/179 |
| 2009/0082829 A1 | 3/2009 | Panken et al. | |
| 2009/0112281 A1 | 4/2009 | Miyazawa et al. | |
| 2009/0187222 A1 | 7/2009 | Barker | |
| 2009/0276021 A1 | 11/2009 | Meadows et al. | |
| 2010/0076535 A1 | 3/2010 | Pianca et al. | |
| 2010/0268298 A1 | 10/2010 | Pianca et al. | |
| 2011/0004267 A1 | 1/2011 | Meadows | |
| 2011/0077720 A1 | 3/2011 | Torgerson et al. | |
| 2011/0078900 A1 | 4/2011 | Pianca et al. | |
| 2011/0130817 A1 | 6/2011 | Chen | |
| 2011/0130818 A1 | 6/2011 | Chen | |
| 2011/0201977 A1 | 8/2011 | Tass | |
| 2011/0238129 A1 | 9/2011 | Moffitt et al. | |
| 2011/0313500 A1 | 12/2011 | Barker et al. | |
| 2012/0016378 A1 | 1/2012 | Pianca et al. | |
| 2012/0046710 A1 | 2/2012 | Digiore et al. | |
| 2012/0071949 A1 | 3/2012 | Pianca et al. | |
| 2012/0165911 A1 | 6/2012 | Pianca | |
| 2012/0197375 A1 | 8/2012 | Pianca et al. | |
| 2012/0203316 A1 | 8/2012 | Moffitt et al. | |
| 2012/0203320 A1 | 8/2012 | DiGiore et al. | |
| 2012/0203321 A1 | 8/2012 | Moffitt et al. | |
| 2012/0274273 A1 | 11/2012 | Jacobs et al. | |
| 2012/0316615 A1 | 12/2012 | DiGiore et al. | |
| 2013/0105071 A1 | 5/2013 | DiGiore et al. | |
| 2013/0218239 A1 | 8/2013 | Grill et al. | |
| 2013/0231713 A1 | 9/2013 | De Ridder | |
| 2013/0289385 A1 | 10/2013 | Lozano et al. | |
| 2013/0317583 A1 | 11/2013 | Pianca | |
| 2013/0317585 A1 | 11/2013 | Barker | |
| 2013/0317586 A1 | 11/2013 | Pianca | |
| 2013/0317587 A1 | 11/2013 | Barker | |
| 2013/0317588 A1 | 11/2013 | Howard et al. | |
| 2014/0025133 A1 | 1/2014 | Lozano | |
| 2014/0081349 A1 | 3/2014 | Lee et al. | |
| 2014/0277281 A1* | 9/2014 | Grandhe | A61N 1/36146 607/59 |
| 2016/0030666 A1 | 2/2016 | Lozano et al. | |

OTHER PUBLICATIONS

Office Communication from the International Searching Authority for Application PCT/US2015/051486 dated Jan. 13, 2016, 6 pages.
International Search Report and Written Opinion for PCT/US2015/051486 dated Mar. 30, 2016.

* cited by examiner

SYSTEMS AND METHODS FOR PROVIDING THERAPY USING ELECTRICAL STIMULATION TO DISRUPT NEURONAL ACTIVITY

CROSS-REFERENCE TO RELATED APPLICATIONS

This application claims the benefit under 35 U.S.C. §119 (e) of U.S. Provisional Patent Application Ser. No. 62/053,589 filed Sep. 22, 2014, which is incorporated herein by reference.

FIELD

The present invention is directed to the area of electrical stimulation systems and methods of using the systems. The present invention is also directed to systems and methods for providing therapy using electrical stimulation generated from electrical stimulation systems to disrupt undesired neural activity through desynchronisation of action potential propagation along patient tissue.

BACKGROUND

Implantable electrical stimulation systems have proven therapeutic in a variety of diseases and disorders. For example, spinal cord stimulation systems have been used as a therapeutic modality for the treatment of chronic pain syndromes. Peripheral nerve stimulation has been used to treat chronic pain syndrome and incontinence, with a number of other applications under investigation. Functional electrical stimulation systems have been applied to restore some functionality to paralyzed extremities in spinal cord injury patients.

Stimulators have been developed to provide therapy for a variety of treatments. A stimulator can include an implantable pulse generator (IPG), one or more leads, and an array of stimulator electrodes on each lead. The stimulator electrodes are in contact with or near the nerves, muscles, or other tissue to be stimulated. The pulse generator generates electrical pulses that are delivered by the electrodes to body tissue.

BRIEF SUMMARY

In one embodiment, an electrical stimulation system includes an implantable control module that is configured and arranged for implantation in a body of a patient and that includes a processor. The control module is configured and arranged to provide electrical stimulation signals to at least one electrical stimulation lead coupled to the implantable control module for stimulation of patient tissue to treat patient pain. A first electrode is disposed on the at least one electrical stimulation lead in the spinal cord of the patient and is configured and arranged to communicate with the processor and to generate a first effective electric field suitable for stimulating patient tissue using the electrical stimulation signals provided from the control module. A second electrode is disposed on the at least one electrical stimulation lead in the spinal cord of the patient and is configured and arranged to communicate with the processor and to generate a second effective electric field suitable for stimulating patient tissue using the electrical stimulation signals provided from the control module. The second effective electric field is time-delayed from the first effective electric field such that the second effective electric field is out of phase with the first effective electric field.

In at least some embodiments, the electrical stimulation system includes a sensor in communication with the processor, the sensor configured and arranged for monitoring patient theta-band activity and detecting frequency shifts. In at least some embodiments, the control module is configured and arranged to provide electrical stimulation signals to the first electrode and the second electrode in response to a first detected shift in frequency of the theta-band activity. In at least some embodiments, the processor is configured and arranged for determining the time delay between the electrical stimulation signals within the first effective electric field and the electrical stimulation signals within the second effective electric field based on the first detected shift in frequency of the theta-band activity. In at least some embodiments, the control module is configured and arranged to provide the electrical stimulation signals to the first electrode and the second electrode in response to a first detected shift in frequency of the theta-band activity at frequencies that are no more than 2 Hz above or below the frequency of the first detected shift in frequency of the theta-band activity. In at least some embodiments, the control module is configured and arranged to adjust at least one of amplitude, frequency, impedance, voltage, or pulse width of the electrical stimulation signals provided to the first electrode and the second electrode in response to a second detected shift in frequency of the theta-band activity. In at least some embodiments, the control module is configured and arranged to terminate the electrical stimulation signals provided to the first electrode and the second electrode in response to a third detected shift in frequency of the theta-band activity.

In at least some embodiments, the electrical stimulation system includes a computer model in communication with the processor, the computer model configured and arranged for coordinating with the processor to facilitate the positioning of the first electrode and the second electrode in the spinal cord of the patient. In at least some embodiments, the electrical stimulation system includes a computer model in communication with the processor, the computer model configured and arranged for coordinating with the processor to adjust at least one of amplitude, frequency, impedance, voltage, or pulse width of at least one of the first effective electric field or the second effective electric field.

In at least some embodiments, the electrical stimulation system includes an actuator located external to the patient and in communication with the processor, the actuator configured and arranged for causing the control module to initiate providing the electrical stimulation signals to the at least one electrical stimulation lead.

In at least some embodiments, the electrical stimulation system includes an actuator located external to the patient and in communication with the processor, the actuator configured and arranged for causing the control module to terminate providing the electrical stimulation signals to the at least one electrical stimulation lead.

In another embodiment, an electrical stimulation system includes an implantable control module that is configured and arranged for implantation in a body of a patient and that includes a processor. The control module is configured and arranged to provide electrical stimulation signals to at least one electrical stimulation lead coupled to the implantable control module for stimulation of patient tissue to treat patient pain. A first electrode is disposed on the at least one electrical stimulation lead in the spinal cord of the patient and is configured and arranged to communicate with the processor and to generate a first effective electric field suitable for stimulating patient tissue using the electrical stimulation signals provided from the control module. A second electrode is disposed on the at least one electrical stimulation lead in the spinal cord of the patient and is configured and arranged to communicate with the processor and to generate a second effective electric field suitable for stimulating patient tissue using the electrical stimulation signals provided from the control module. The second effective electric field is coordinated with the first effective electric field and has an overlap in volume of no more than 20% with the first effective electric field.

In at least some embodiments, the second effective electric field does not overlap in volume with the first effective electric field.

In at least some embodiments, the electrical stimulation system includes a computer model in communication with the processor, the computer model configured and arranged for coordinating with the processor to facilitate the positioning of the first electrode and the second electrode in the spinal cord of the patient such that the second effective electric field has an overlap in volume of no more than 20% with the first effective electric field.

In at least some embodiments, the electrical stimulation system includes a computer model in communication with the processor, the computer model configured and arranged for coordinating with the processor to adjust at least one of amplitude, frequency, impedance, voltage, or pulse width of at least one of the first effective electric field or the second effective electric field such that the second effective electric field has an overlap in volume of no more than 20% with the first effective electric field.

In at least some embodiments, the electrical stimulation system includes a sensor in communication with the processor, the sensor configured and arranged for monitoring patient theta-band activity and detecting frequency shills.

In yet another embodiment, an electrical stimulation system includes an implantable control module that is configured and arranged for implantation in a body of a patient and that includes a processor. The control module is configured and arranged to provide electrical stimulation signals to at least one electrical stimulation lead coupled to the implantable control module for stimulation of patient tissue to treat patient pain. A first electrode is disposed on the at least one electrical stimulation lead in the spinal cord of the patient and is configured and arranged to communicate with the processor and to generate a first effective electric field suitable for stimulating a first set of neurons within patient tissue using the electrical stimulation signals provided from the control module. A second electrode is disposed on the at least one electrical stimulation lead in the spinal cord of the patient and is configured and arranged to communicate with the processor and to generate a second effective electric field suitable for stimulating a second set of neurons that is different from the first set of neurons within patient tissue using the electrical stimulation signals provided from the control module. The second effective electric field has an overlap in volume of at least 50% with the first effective electric field.

In at least some embodiments, the second set of target neurons is a subset of the first set of target neurons. In at least some embodiments, the second set of target neurons is mutually exclusive of the first set of target neurons.

In at least some embodiments, the electrical stimulation system includes a sensor in communication with the processor, the sensor configured and arranged for monitoring patient theta-band activity and detecting frequency shifts.

In still yet another embodiment, a non-transient computer-readable medium has processor-executable instructions for electrically stimulating tissue of a patient. The processor-executable instructions when installed onto a control module enable the control module to perform actions, including: generating a first effective electric field suitable for stimulating patient tissue using electrical stimulation signals from a first electrode disposed at a first stimulation location within the patient and coupled to the control module: and generating a second effective electric field suitable for stimulating patient tissue using electrical stimulation signals from a second electrode disposed at a second stimulation location within the patient and coupled to the control module. The second effective electric field is time-delayed from the first effective electric field such that the second effective electric field is out of phase with the first effective electric field.

In another embodiment, a method for electrically stimulating a patient includes advancing a first electrode to a first target stimulation location along the spinal cord of the patient. A second electrode is advanced to a second target stimulation location along the spinal cord of the patient. The first electrode and the second electrode are coupled to a control module. A first effective electric field is generated that is suitable for stimulating patient tissue via the first electrode. The first effective electric field includes electrical stimulation signals generated by the control module. A second effective electric field is generated that is suitable for stimulating patient tissue via the second electrode. The second effective electric field includes electrical stimulation signals generated by the control module. The electrical stimulation signals within the second effective electric field is time-delayed from the electrical stimulation signals within the first effective electric field such that the second effective electric field is out of phase with the first effective electric field.

In yet another embodiment, a lead-based electrical stimulator includes a first electrode and a second electrode implanted into a patient. A processor is disposed in a control module coupled to the first electrode and the second electrode. The processor is for executing processor-readable instructions that enable actions, including: generating a first effective electric field suitable for stimulating patient tissue using electrical stimulation signals from a first electrode disposed at a first stimulation location within the patient and coupled to the control module; and generating a second effective electric field suitable for stimulating patient tissue using electrical stimulation signals from a second electrode disposed at a second stimulation location within the patient and coupled to the control module. The second effective electric field is time-delayed from the first effective electric field such that the second effective electric field is out of phase with the first effective electric field.

In still yet another embodiment, a non-transient computer-readable medium has processor-executable instructions for electrically stimulating tissue of a patient. The processor-executable instructions when installed onto a control module enable the control module to perform actions, including: generating a first effective electric field suitable for stimulating patient tissue using electrical stimulation signals from a first electrode disposed at a first stimulation location within the patient and coupled to the control module; and generating a second effective electric field suitable for stimulating patient tissue using electrical stimulation signals from a second electrode disposed at a second stimulation location within the patient and coupled to the control module. At least one of amplitude, frequency, impedance, voltage, or pulse width of the first effective electric field is different from that of the second effective electric field and is selected based on at least one physical characteristic of stimulated neurons within an overlapping region of the first effective electric field and the second effective electric field.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The present invention is directed to the area of electrical stimulation systems and methods of using the systems. The present invention is also directed to systems and methods for providing therapy using electrical stimulation generated from electrical stimulation systems to disrupt undesired neural activity through desynchronization of action potential propagation along patient tissue.

Suitable implantable electrical stimulation systems include, but are not limited to, an electrode lead ("lead") with one or more electrodes disposed on a distal end of the lead and one or more terminals disposed on one or more proximal ends of the lead. Leads include, for example, deep brain stimulation leads, percutaneous leads, paddle leads, and cuff leads. Examples of electrical stimulation systems with leads are found in, for example, U.S. Pat. Nos. 6,181,969; 6,516,227; 6,609,029; 6,609,032; 6,741,892; 7,244,150; 7,450,997; 7,672,734; 7,761,165; 7,783,359; 7,792,590; 7,809,446; 7,949,395; 7,974,706; 8,175710; 8,224,450; 8,271,094; 8,295,944; 8,364,278; and 8,391,985; U.S. Patent Applications Publication Nos. 2007/0150036; 2009/0187222; 2009/0276021; 2010/0076535; 2010/0268298; 2011/0004267; 2011/0078900; 2011/0130817; 2011/0130818; 2011/0238129; 2011/0313500; 2012/0016378; 2012/0046710; 2012/0071949; 2012/0165911; 2012/0197375; 2012/0203316; 2012/0203320; 2012/0203321; 2012/0316615; and 2013/0105071; and U.S. patent application Ser. Nos. 12/177,823 and 13/750,725, all of which are incorporated by reference.

Figure 1:
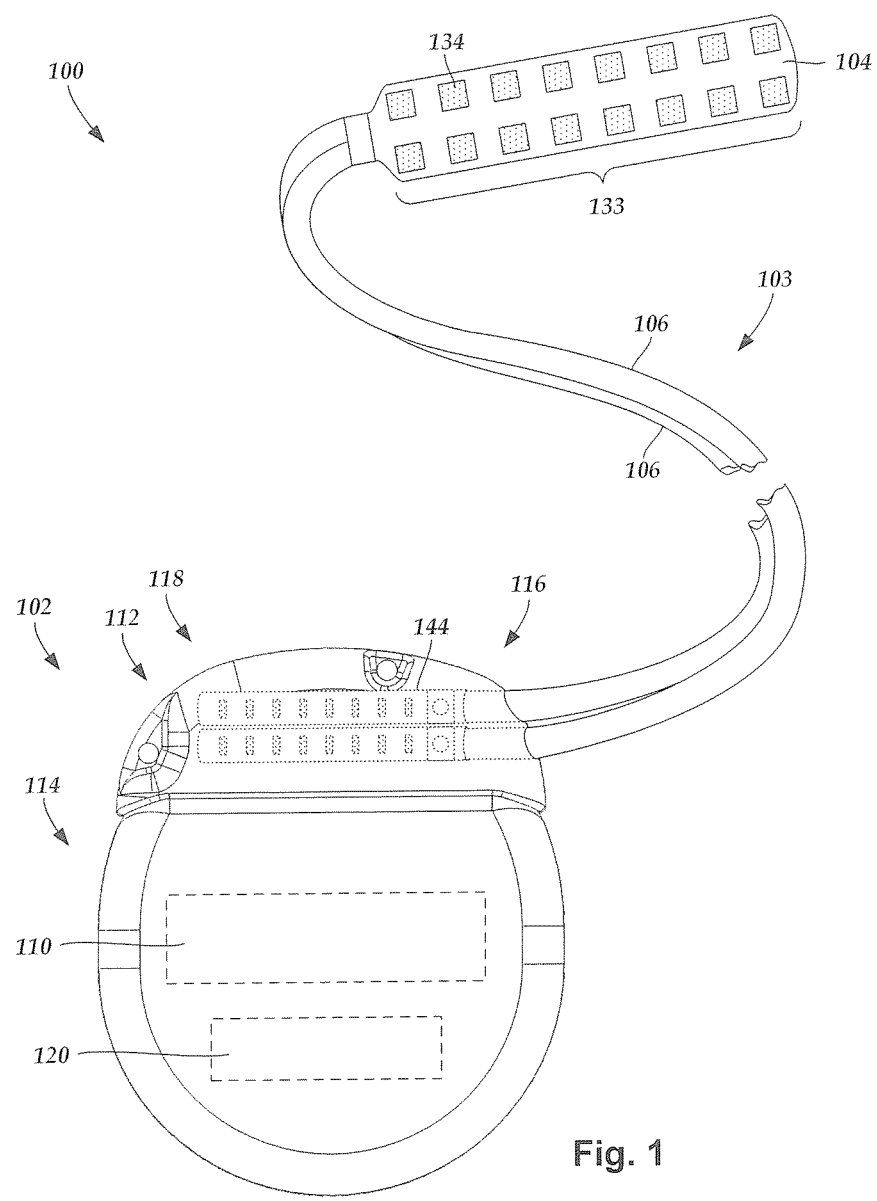
FIG. 1 is a schematic view of one embodiment of an electrical stimulation system that includes a paddle lead electrically coupled to a control module, according to the invention.

FIG. 1 illustrates schematically one embodiment of an electrical stimulation system 100. The electrical stimulation system includes a control module (e.g., a device that includes a stimulator or pulse generator) 102 and a lead 103 coupleable to the control module 102. The lead 103 includes a paddle body 104 and one or more lead bodies 106. In FIG. 1, the lead 103 is shown having two lead bodies 106. It will be understood that the lead 103 can include any suitable number of lead bodies including, for example, one, two, three, four, five, six, seven, eight or more lead bodies 106. An array of electrodes 133, such as electrode 134, is disposed on the paddle body 104, and an array of terminals (e.g., 210 in FIG. 2A-2B) is disposed along each of the one or more lead bodies 106.

It will be understood that the electrical stimulation system can include more, fewer, or different components and can have a variety of different configurations including those configurations disclosed in the electrical stimulation system references cited herein. For example, instead of a paddle body, the electrodes can be disposed in an array at or near the distal end of a lead body forming a percutaneous lead.

Figure 2:
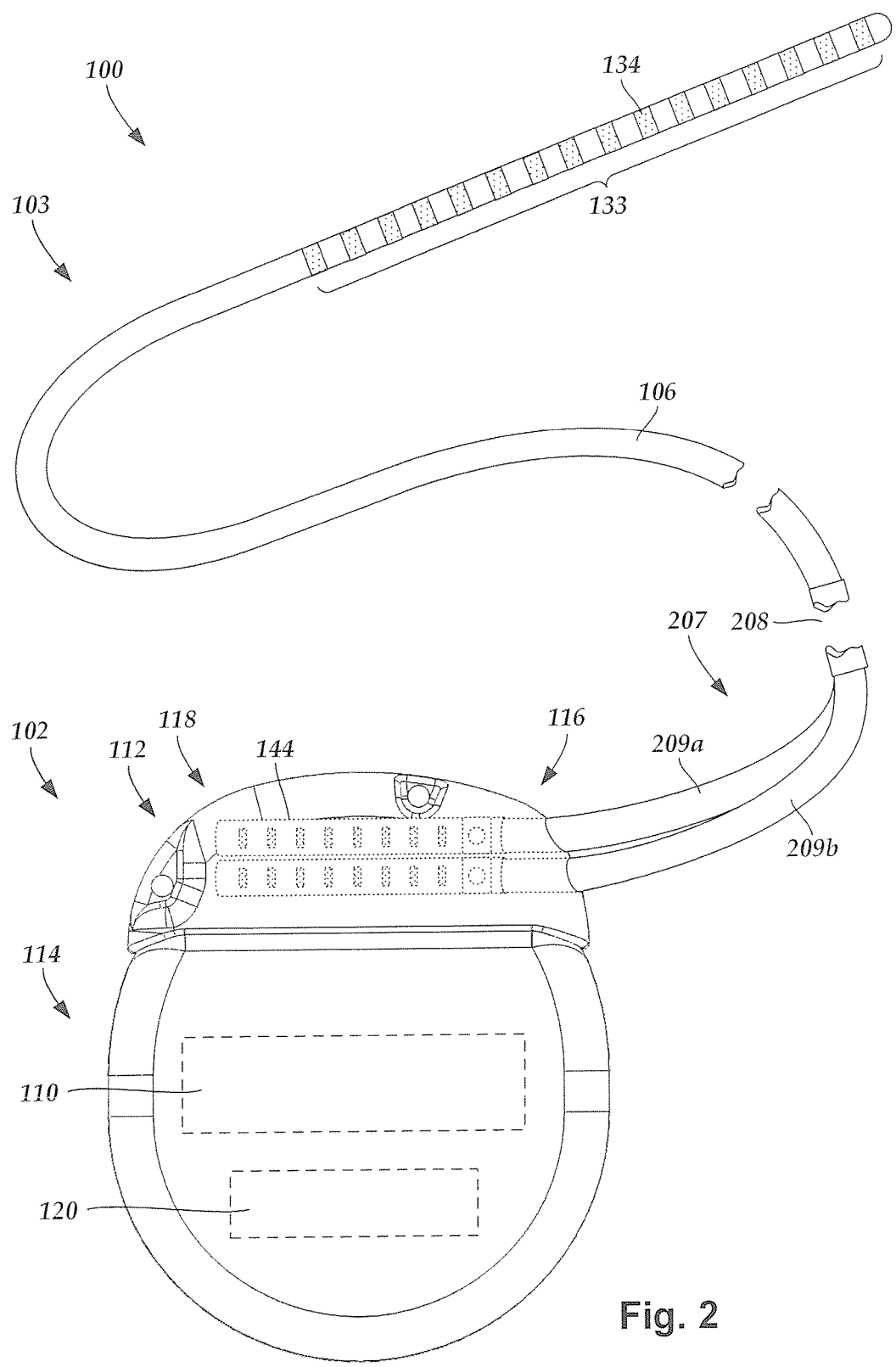
FIG. 2 is a schematic view of one embodiment of an electrical stimulation system that includes a percutaneous lead electrically coupled to a control module, according to the invention.

FIG. 2 illustrates schematically another embodiment of the electrical stimulation system 100, where the lead 103 is a percutaneous lead. In FIG. 2, the electrodes 134 are shown disposed along the one or more lead bodies 106. In at least some embodiments, the lead 103 is isodiametric along a longitudinal length of the lead body 106.

Referring to both FIG. 1 and FIG. 2, the lead 103 can be coupled to the control module 102 in any suitable manner. In at least some embodiments, the lead 103 couples directly to the control module 102. In at least some other embodiments, the lead 103 couples to the control module 102 via one or more intermediate devices (300 in FIGS. 3A-3B). For example, in at least some embodiments one or more lead extensions 324 (see e.g., FIG. 3B) can be disposed between the lead 103 and the control module 102 to extend the distance between the lead 103 and the control module 102. Other intermediate devices may be used in addition to, or in lieu of, one or more lead extensions including, for example, a splitter, an adaptor, or the like or combinations thereof. It will be understood that, in the case where the electrical stimulation system 100 includes multiple elongated devices disposed between the lead 103 and the control module 102, the intermediate devices may be configured into any suitable arrangement.

In FIG. 2, the electrical stimulation system 100 is shown having a splitter 207 configured and arranged for facilitating coupling of the lead 103 to the control module 102. The splitter 207 includes a splitter connector 208 configured to couple to a proximal end of the lead 103, and one or more splitter tails 209a and 209b configured and arranged to couple to the control module 102 (or another splitter, a lead extension, an adaptor, or the like).

Referring to both FIG. 1 and FIG. 2, the control module 102 typically includes a connector housing 112, or "header," and a sealed electronics housing 114. An electronic subassembly 110 and an optional power source 120 are disposed in the sealed electronics housing 114. The connector housing 112 is disposed along a portion of an exterior surface of the sealed electronics housing 114 and includes a first end 116 and an opposing second end 118.

A control-module connector 144 is disposed in the connector housing 112. The control-module connector 144 is configured and arranged to receive, either directly or indirectly, a portion of the lead 103 and make an electrical connection between the lead 103 and the electronic subassembly 110 of the control module 102.

The electrical stimulation system, or components of the electrical stimulation system, including the paddle body 104, the one or more of the lead bodies 106, and the control module 102, are typically implanted into the body of a patient. The electrical stimulation system can be used for a variety of applications including, but not limited to deep brain stimulation, neural stimulation, spinal cord stimulation, muscle stimulation, and the like.

The electrodes 134 can be formed using any conductive, biocompatible material. Examples of suitable materials include metals, alloys, conductive polymers, conductive carbon, and the like, as well as combinations thereof. In at least some embodiments, one or more of the electrodes 134 are formed from one or more of: platinum, platinum iridium, palladium, palladium rhodium, or titanium.

Any suitable number of electrodes 134 can be disposed on the lead including, for example, four, five, six, seven, eight, nine, ten, eleven, twelve, fourteen, sixteen, twenty-four, thirty-two, or more electrodes 134. In the case of paddle leads, the electrodes 134 can be disposed on the paddle body 104 in any suitable arrangement. FIG. 1, the electrodes 134 are arranged into two columns, where each column has eight electrodes 134.

The electrodes of the paddle body 104 (or one or more lead bodies 106) are typically disposed in, or separated by, a non-conductive, biocompatible material such as, for example, silicone, polyurethane, polyetheretherketone ("PEEK"), epoxy, and the like or combinations thereof. The one or more lead bodies 106 and, if applicable, the paddle body 104 may be formed in the desired shape by any process including, for example, molding (including injection molding), casting, and the like. The non-conductive material typically extends from the distal ends of the one or more lead bodies 106 to the proximal end of each of the one or more lead bodies 106.

In the case of paddle leads, the non-conductive material typically extends from the paddle body 104 to the proximal end of each of the one or more lead bodies 106. Additionally, the non-conductive, biocompatible material of the paddle body 104 and the one or more lead bodies 106 may be the same or different. Moreover, the paddle body 104 and the one or more lead bodies 106 may be a unitary structure or can be formed as two separate structures that are permanently or detachably coupled together.

Figure 3A:
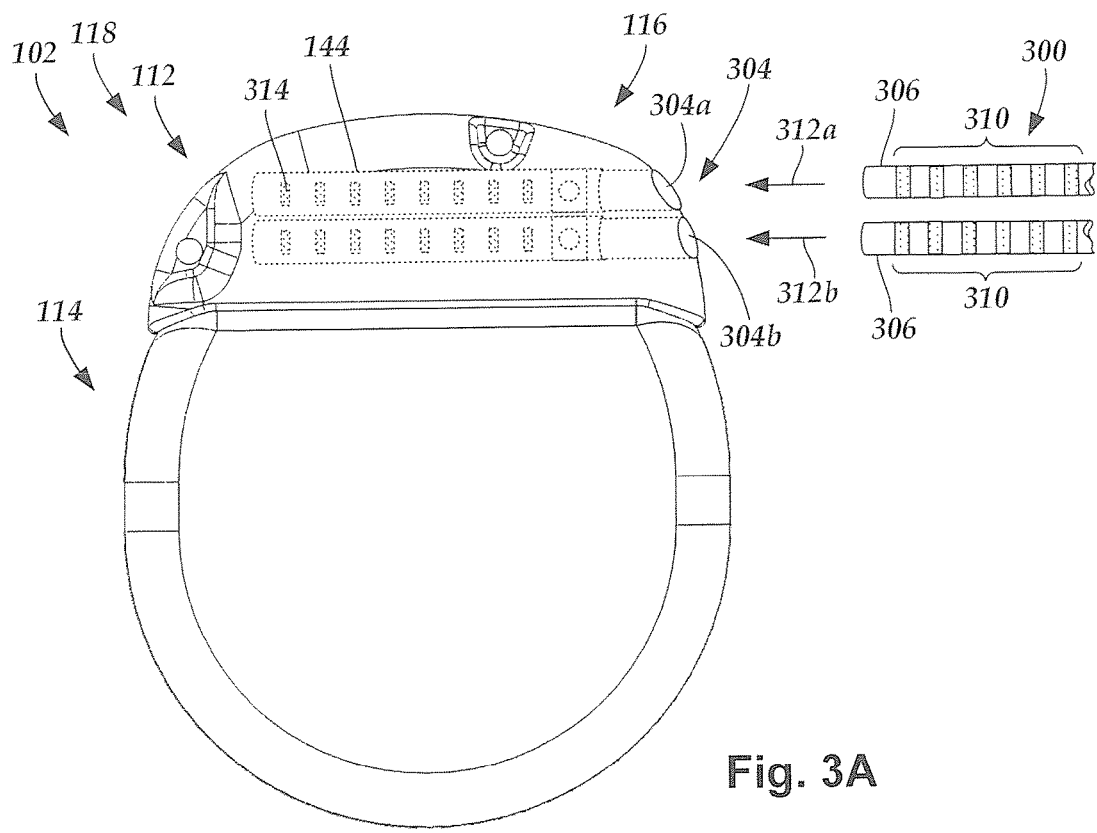
FIG. 3A is a schematic view of one embodiment of the control module of FIG. 1 and two elongated members of a lead assembly, the control module defining two lead-assembly ports configured for receiving the two elongated members of the lead assembly, the control module, according to the invention.
Figure 3B:
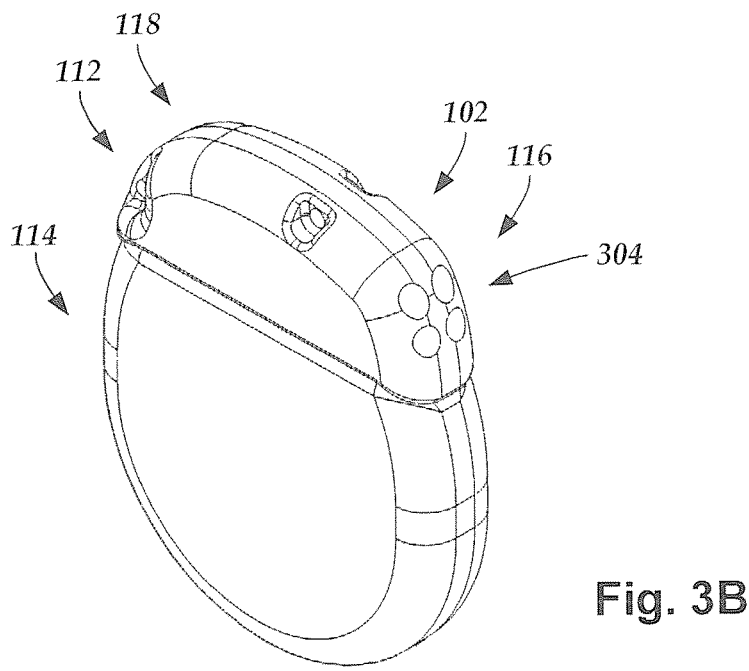
FIG. 3B is a schematic view of another embodiment of the control module of FIG. 1, the control module defining four lead-assembly ports configured for receiving up to four elongated members of one or more lead assemblies, the control module, according to the invention.

Terminals (e.g., 310 in FIGS. 3A-3B) are typically disposed along the proximal end portion of the one or more lead bodies 106 of the electrical stimulation system 100 (as well as along proximal end portions of any splitters, lead extensions, adaptors, or the like) for electrical connection to corresponding connector contacts (e.g., 314 in FIGS. 3A-3B). The connector contacts are disposed in connectors (e.g., 144 in FIGS. 1-3B; and 322 FIG. 3B) which, in turn, are disposed on, for example, the control module 102 (or along a distal end portion of a lead extension, a splitter, an adaptor, or the like). Electrically-conductive wires, cables, or the like ("conductors") (not shown) extend from, in the case of lead bodies, the terminals to the electrodes 134. In the case of intermediate devices (e.g., lead extensions, adaptors, splitters, or the like), the conductors extend from terminals to connector contacts of connectors (see e.g., connector contacts 340 of lead-extension connector 322 of FIG. 3C). Typically, one or more electrodes 134 are electrically coupled to each terminal. In at least some embodiments, each terminal is only connected to one electrode 134.

The conductors may be embedded in the non-conductive material of the lead body 106 (or other elongated members, such as lead extensions, splitters, adaptors, or the like) or can be disposed in one or more lumens (not shown) extending along the lead body 106 (or other elongated member). In some embodiments, there is an individual lumen for each conductor. In other embodiments, two or more conductors extend through a lumen. There may also be one or more stylet lumens (not shown) that open at, or near, the proximal end of the one or more lead bodies 106, for example, for inserting a stylet to facilitate placement of the one or more lead bodies 106 within a body of a patient. Additionally, there may be one or more lumens (not shown) that open at, or near, the distal end of the one or more lead bodies 106 (or other elongated members), for example, for infusion of drugs or medication into the site of implantation. In at least one embodiment, the one or more lumens are flushed continually, or on a regular basis, with saline, epidural fluid, or the like. In at least some embodiments, the one or more lumens are permanently or removably sealable along distal ends of the lumens.

FIG. 3A is a schematic side view of one embodiment of proximal end portions of two elongated members 306 of a lead assembly 300 configured and arranged for coupling to one embodiment of the control-module connector 144. The elongated members 306 of the lead assembly 300 may include, for example, one or more of the lead bodies (e.g., the lead bodies 106 of FIG. 1 or FIG. 2), one or more intermediate devices (e.g., the splitter 207, the lead extension 324 of FIG. 3C, an adaptor, or the like or combinations thereof), or a combination thereof.

The control-module connector 144 defines at least one lead-assembly port 304 into which a proximal end portion of the lead assembly 300 can be inserted, as shown by directional arrows 312a and 312b. In FIG. 3A (and in other figures), the connector housing 112 is shown having two lead-assembly ports 304a and 304b. The connector housing 112 can define any suitable number of lead-assembly ports including, for example, one, two, three, four, five, six, seven, eight, or more lead-assembly ports. FIG. 3B illustrates an alternate embodiment of the control module 102 with four lead-assembly ports 304 disposed in the connector housing 112. The lead-assembly ports 304 shown in each of FIGS. 3A-3B extend from the first end 116 of the connector housing 112.

As shown in FIG. 3A, the control-module connector 144 also includes a plurality of connector contacts, such as connector contact 314, disposed within each lead-assembly port 304a and 304b. When the one or more lead assemblies 300 are inserted into the one or more lead-assembly ports 304a and 304b, the connector contacts 314 can be aligned with terminals 310 disposed along the proximal end portion(s) of the one or more lead assemblies 300 to electrically couple the control module 102 to the electrodes (134 of FIG. 1 or 2). Examples of connectors in control modules are found in, for example, U.S. Pat. Nos. 7,244,150 and 8,224,450 which are incorporated by reference.

Figure 3C:
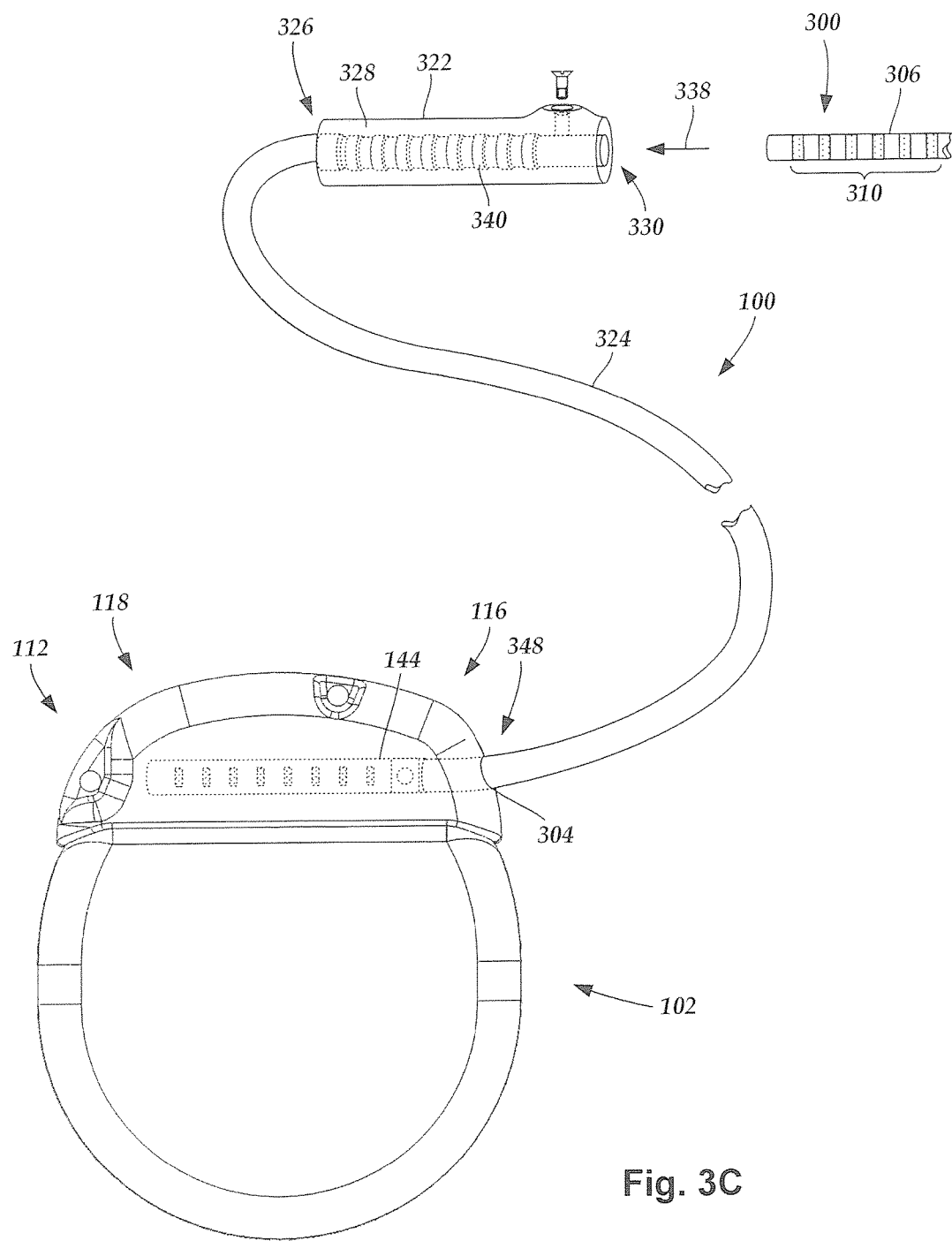
FIG. 3C is a schematic view of one embodiment of an elongated member of the lead assembly of FIG. 3A and a lead extension coupled to the control module of FIG. 1, the lead extension configured to receive the elongated member, according to the invention.

FIG. 3C is a schematic side view of another embodiment of the electrical stimulation system 100. The electrical stimulation system 100 includes a lead extension 324 that is configured and arranged to couple one or more elongated members (e.g., one or more lead bodies, splitters, adaptors, another lead extension, or the like or combinations thereof) of the lead assembly 300 to the control module 102. In FIG. 3B, the lead extension 324 is shown coupled to a single lead-assembly port 304 defined in the control-module connector 144. Additionally, the lead extension 324 is shown configured and arranged to couple to a single elongated member 306. In alternate embodiments, the lead extension 324 is configured and arranged to couple to multiple lead-assembly ports 304 defined in the control-module connector 144, or to receive multiple elongated members, or both.

A lead-extension connector 322 is disposed on the lead extension 324. In FIG. 3B, the lead-extension connector 322 is shown disposed along a distal end portion 326 of the lead extension 324. The lead-extension connector 322 includes a connector housing 328. The connector housing 328 defines at least one lead-assembly port 330 into which terminals 310 of the elongated device can be inserted, as shown by directional arrow 338. The connector housing 328 also includes a plurality of connector contacts, such as connector contact 340. When the elongated device 306 is inserted into the lead-assembly port 330, the connector contacts 240 disposed in the connector housing 328 can be aligned with the terminals 310 of the elongated device to electrically couple the lead extension 324 to the electrodes (134 of FIGS. 1 and 2) disposed along the lead (103 in FIGS. 1 and 2).

In at least some embodiments, a proximal end portion 348 of the lead extension 324 is similarly configured and arranged as a proximal end portion of the lead 103 (or other elongated member 306). The lead extension 324 may include a plurality of conductors (see e.g., 420 in FIG. 4B) that electrically couple the connector contacts 340 to the proximal end portion 348 of the lead extension 324 that is opposite to the distal end portion 326. In at least some embodiments, the conductors disposed in the lead extension 324 can be electrically coupled to a plurality of terminals (not shown) disposed along the proximal end portion 348 of the lead extension 324. In at least some embodiments, the proximal end portion 348 of the lead extension 324 is configured and arranged for insertion into a connector disposed in another lead extension (or another intermediate device). In other embodiments (and as shown in FIG. 3B), the proximal end portion 348 of the lead extension 324 is configured and arranged for insertion into the control-module connector 144.

Figure 4:
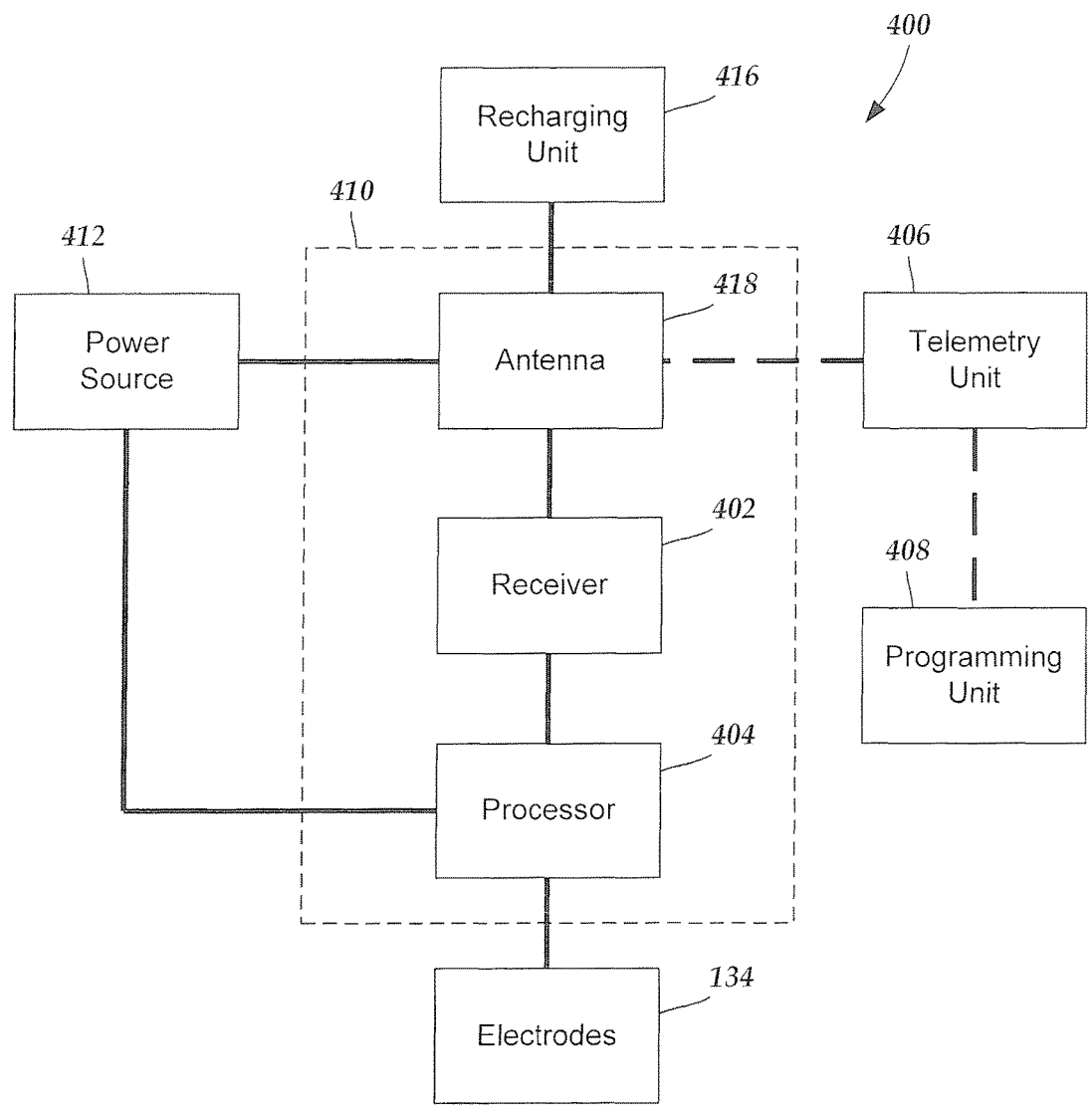
FIG. 4 is schematic overview of one embodiment of components of a stimulation system, including an electronic subassembly disposed within a control module, according to the invention.

FIG. 4 is a schematic overview of one embodiment of components of an electrical stimulation system 400 including an electronic subassembly 410 disposed within a control module. It will be understood that the electrical stimulation system can include more, fewer, or different components and can have a variety of different configurations including those configurations disclosed in the stimulator references cited herein.

Some of the components (for example, a power source 412, an antenna 418, a receiver 402, and a processor 404) of the electrical stimulation system can be positioned on one or more circuit boards or similar carriers within a sealed housing of an implantable pulse generator, if desired. Any power source 412 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Pat. No. 7,437,193, incorporated herein by reference.

As another alternative, power can be supplied by an external power source through inductive coupling via the optional antenna 418 or a secondary antenna. The external power source can be in a device that is mounted on the skin of the user or in a unit that is provided near the user on a permanent or periodic basis.

If the power source 412 is a rechargeable battery, the battery may be recharged using the optional antenna 418, if desired. Power can be provided to the battery for recharging by inductively coupling the battery through the antenna to a recharging unit 416 external to the user. Examples of such arrangements can be found in the references identified above.

In one embodiment, electrical stimulation signals are emitted by the electrodes 134 on the paddle or lead body to stimulate nerve fibers, muscle fibers, or other body tissues near the electrical stimulation system. The processor 404 is generally included to control the timing and electrical characteristics of the electrical stimulation system. For example, the processor 404 can, if desired, control one or more of the timing, frequency, strength, duration, and waveform of the pulses. In addition, the processor 404 can select which electrodes can be used to provide stimulation, if desired. In some embodiments, the processor 404 selects which electrode(s) are cathodes and which electrode(s) are anodes. In some embodiments, the processor 404 is used to identify which electrodes provide the most useful stimulation of the desired tissue.

Any processor can be used and can be as simple as an electronic device that, for example, produces pulses at a regular interval or the processor can be capable of receiving and interpreting instructions from an external programming unit 408 that, for example, allows modification of pulse characteristics. In the illustrated embodiment, the processor 404 is coupled to a receiver 402 which, in turn, is coupled to the optional antenna 418. This allows the processor 404 to receive instructions from an external source to, for example, direct the pulse characteristics and the selection of electrodes if desired.

In one embodiment, the antenna 418 is capable of receiving signals (e.g., RF signals) from an external telemetry unit 406 which is programmed by the programming unit 408. The programming unit 408 can be external to, or part of, the telemetry unit 406. The telemetry unit 406 can be a device that is worn on the skin of the user or can be carried by the user and can have a form similar to a pager, cellular phone, or remote control, if desired. As another alternative, the telemetry unit 406 may not be worn or carried by the user but may only be available at a home station or at a clinician's office. The programming unit 408 can be any unit that can provide information to the telemetry unit 406 for transmission to the electrical stimulation system 400. The programming unit 408 can be part of the telemetry unit 406 or can provide signals or information to the telemetry unit 406 via a wireless or wired connection. One example of a suitable programming unit is a computer operated by the user or clinician to send signals to the telemetry unit 406.

The signals sent to the processor 404 via the antenna 418 and the receiver 402 can be used to modify or otherwise direct the operation of the electrical stimulation system. For example, the signals may be used to modify the pulses of the electrical stimulation system such as modifying one or more of pulse duration, pulse frequency, pulse waveform, and pulse strength. The signals may also direct the electrical stimulation system 400 to cease operation, to start operation, to start charging the battery, or to stop charging the battery. In other embodiments, the stimulation system does not include the antenna 418 or receiver 402 and the processor 404 operates as programmed.

Optionally, the electrical stimulation system 400 may include a transmitter (not shown) coupled to the processor 404 and the antenna 418 for transmitting signals back to the telemetry unit 406 or another unit capable of receiving the signals. For example, the electrical stimulation system 400 may transmit signals indicating whether the electrical stimulation system 400 is operating properly or not or indicating when the battery needs to be charged or the level of charge remaining in the battery. The processor 404 may also be capable of transmitting information about the pulse characteristics so that a user or clinician can determine or verify the characteristics.

Figure 5:
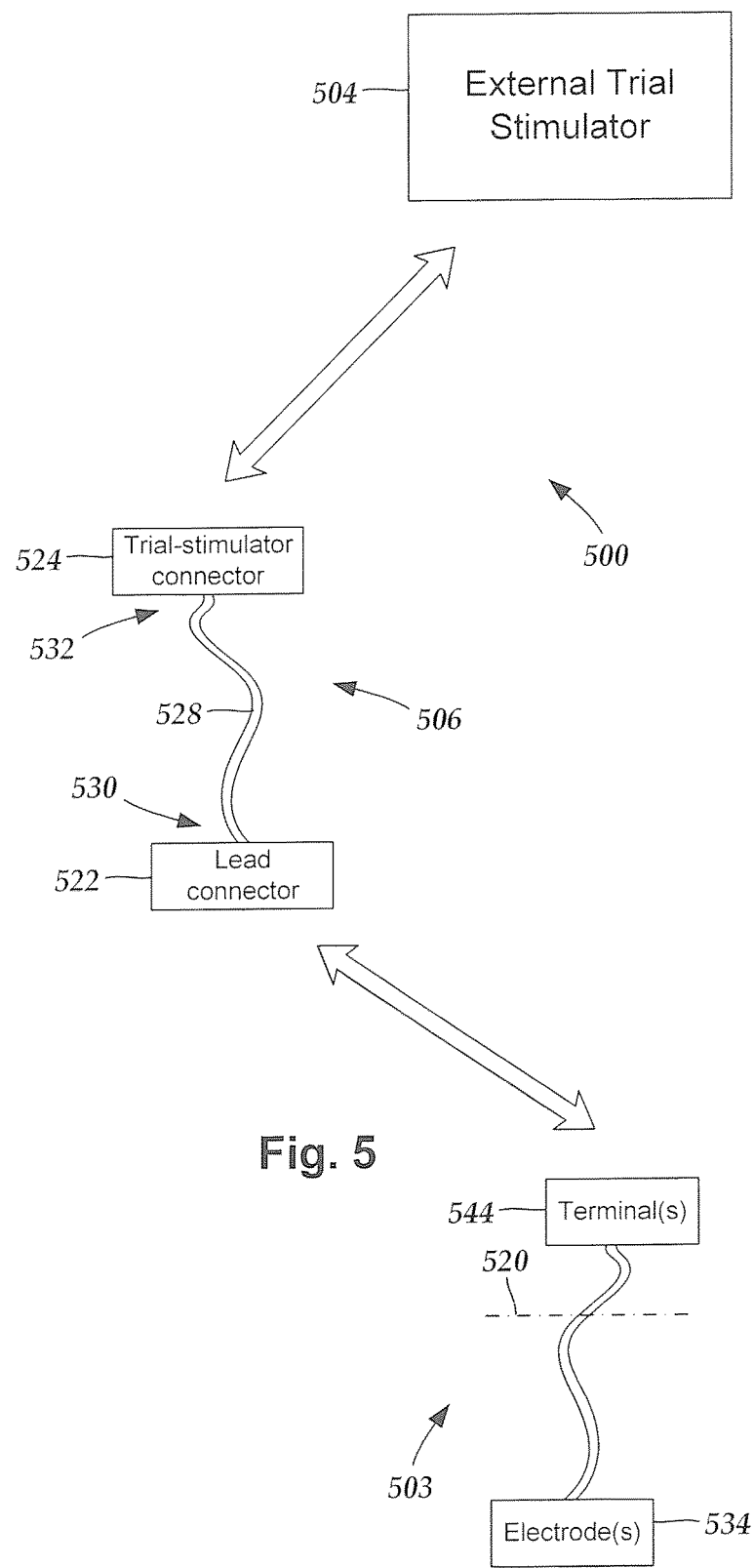
FIG. 5 is a schematic view of one embodiment of a trial stimulation system that includes a lead that is at least partially inserted into a patient and is coupleable to an external trial stimulator, according to the invention.

Turning to FIG. 5, providing therapy using electrical stimulation may be a long-term process. Consequently, at least some stimulation systems provide stimulation (via one or more implanted leads) to the patient over an extended period of time, such as the operational lifetime of the system, the remaining lifetime of the patient, or at least 0.5, 1, 5, 10, 15, 20, or more years.

In some instances, the potential efficacy of electrical stimulation for a particular patient is tested prior to implantation. One way to test efficacy is to perform a trial stimulation (e.g., a percutaneous nerve evaluation, or the like), whereby an electrode-including distal portion of a lead (and, optionally, one or more lead extensions) is temporarily inserted into the patient. The proximal portion of the lead (or lead extension) can then be electrically coupled to a trial stimulator that is disposed external to the patient to perform trial stimulations using the one or more electrodes. Once efficacy is established, the trial stimulation system can be removed and replaced with another lead and control module (see e.g., FIG. 1 or 2).

The trial stimulations may continue for a short period (e.g., 3-10 days) where the patient is sent home with the trial stimulation system to assess the effectiveness of the therapy to determine if a permanent implanted system will be effective in treating the medical condition. During the trial stimulations, the proximal portion of the lead (or the proximal portion of a lead extension coupled to the lead) can be coupled directly to the trial stimulation. Alternately, the lead can be coupled to the trial stimulator by coupling the proximal portion of the lead (or the proximal portion of a lead extension coupled to the lead) to an operating room cable ("cable") that, in turn, is electrically coupled to the trial stimulator.

FIG. 5 is a schematic view of one embodiment of a trial stimulation system 500 that includes a lead 503, an external trial stimulator 504, and one or more cables 506 that couple the lead 503 to the external trial stimulator 504. The lead 503 includes one or more electrodes 534 and one or more terminals 544. During operation, the electrode(s) 534 are disposed internal to the patient, while the terminal(s) 544 remain external to the patient, as shown in FIG. 5 by a line 520 schematically representing patient skin. In alternate embodiments, the lead may be coupled to a lead extension, where the entire lead and a distal portion of the lead extension are disposed in the patient while lead extension terminals remain external to the patient.

The terminal(s) 512 are configured and arranged to couple the electrode(s) 534 to the external trial stimulator 504. In at least some embodiments, a lead connector 322 of the cable 506 is configured and arranged to couple to the terminal(s) 544 of the lead 503 (or lead extension) and a trial stimulator connector 524 of the cable 506 is configured and arranged to couple to the external trial stimulator 504.

Figure 6:
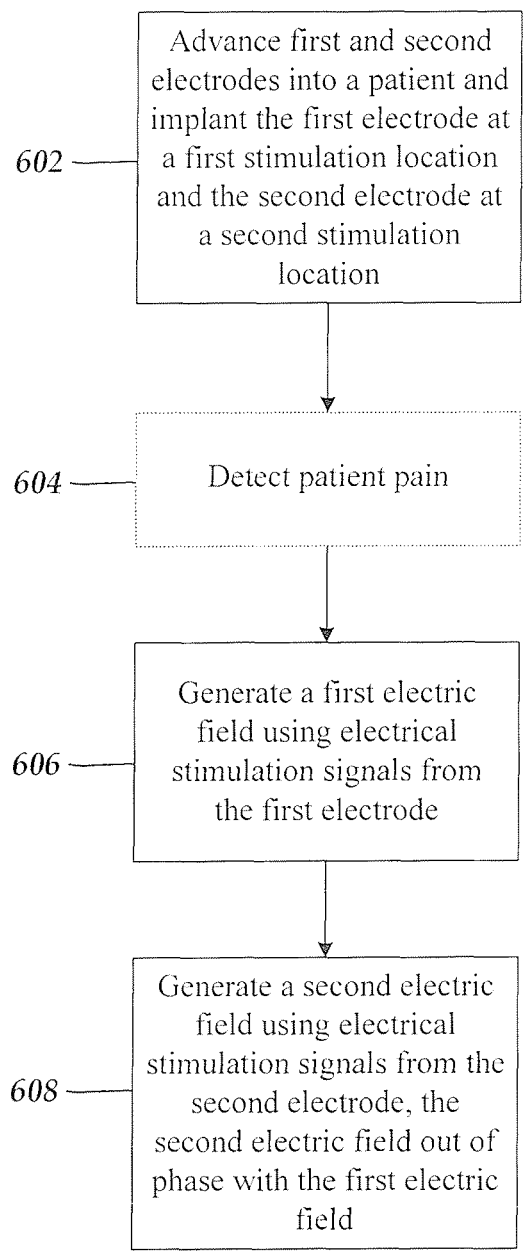
FIG. 6 is a flowchart of one embodiment of a technique for disrupting undesired neural activity through desynchronization of action potential propagation along patient tissue, according to the invention.

Turning to FIG. 6, electrical stimulation (for either long-term stimulation or for trial stimulation) typically involves delivering electrical stimulation signals to a target stimulation location at a site on or near a group of target neurons. The size, intensity, and character of the stimulation may be controlled by adjusting the stimulation parameters (e.g., amplitude, frequency, impedance, voltage, pulse width, or the like) of the electrical stimulation signals. The stimulation may, in some cases, reduce, or even eliminate patient pain.

Patient pain may be identified by any suitable technique including, for example, using a pain measurement scale, patient feedback, a change in one or more monitored pain indicators, or the like. One pain indicator that may be identifiable and observable is a frequency shift in the patient's theta wave activity. It has been shown that frequency shifts in a patient's theta wave activity (e.g., approximately 4 Hz to 8 Hz) may indicate the presence of patient pain. Observed shifts in the frequencies of theta wave activity have been shown to correlate to an undesired neuronal activity (e.g., propagation of action potentials along one or more neural pathways). While not wishing to be held to any particular theory, electrical stimulation may provide therapy to a patient by disrupting undesired neural activity through desynchronization of action potential propagation along patient tissue.

Frequency shifts may include, for example, a shift of at least 0.2 Hz, 0.5 Hz, 0.8 Hz, 1 Hz, 2 Hz, 3 Hz, 4 Hz, 5 Hz, or more. Frequency shifts may include a shift to a particular frequency or frequency range. Frequency shifts may include a change in a pattern of the theta-wave activity. The frequency shifts may be observed using any sensor suitable recording of electrical activity, such as via electroencephalography, or other similar technique. The measured activity can be measured against a known (e.g., previously-recorded) patient base line reading, or compared to a known population, or both.

In at least some embodiments, the patient (or medical practitioner) may be able to initiate stimulation, as needed. For example, the patient (or medical practitioner) may be able to initiate stimulation in response to patient pain by using an actuator (e.g., a switch) that is external to the patient and that is in communication with the processor of the control module.

The stimulation may last for a set period of time (e.g., a minute, an hour, a day, a week, or longer). Alternatively, the stimulation may last until it is manually terminated (e.g., by the patient or the medical practitioner). As discussed below the stimulation may also be terminated automatically in response to feedback.

In some embodiments, one or more pain indicators are monitored. For example, in some embodiments, neural activity within the patient's theta-wave band is monitored (e.g., via one or more sensors in communication with the one or more control modules). In which case, the electrical stimulation may be intermittently performed in response to an observed pain indicator, such as a frequency shift in the theta band. In at least some embodiments, the system includes a sensor that is in communication with the processor and that senses a pain indicator, such as frequency shifts in the theta band and signals initiation of electrical stimulation in response to the observed frequency shift.

In some embodiments, the system employs feedback to adjust one or more stimulation parameters (e.g., amplitude, frequency, impedance, voltage, pulse width, or the like) after a period of stimulation. For example, stimulation may be adjusted based on an observed change in theta-wave activity towards or away from a particular undesired observed frequency or frequency range, or towards or away from a particular desired frequency or frequency range.

In some embodiments, the system employs feedback to terminate stimulation.

Termination of stimulation may be in response to changes in the patient's theta-wave band after a period of stimulation. For example, stimulation may be terminated upon a return to the patient's base line theta-wave activity, or in response to a move away from a particular undesired observed frequency or frequency range.

In at least some embodiments, the undesired neuronal activity is disrupted using two or more electrodes (or two or more sets of electrodes). As discussed below in more detail, electrical stimulation signals propagating through the two or more electrodes (or sets of electrodes) may be coordinated with time delays, or different stimulation parameters, or both. The two or more electrodes (or sets of electrodes) can either be in close physical proximity to one another, or physically spaced-apart from one another. The electrodes may be disposed along a single implanted lead, or along multiple implanted leads. When multiple leads are utilized, the multiple leads may be coupled to the same control module, or to separate control modules in communication with one another (to coordinate the stimulation timing and/or stimulation parameters).

The two or more electrodes (or sets of electrodes) may be implanted at the same target stimulation location or along two different target stimulation locations within the patient. In at least some embodiments, the two or more electrodes (or sets of electrodes) are implanted along the patient's spinal cord. When the two or more electrodes (or sets of electrodes) are implanted along the patient's spinal cord, the two or more electrodes (or sets of electrodes) may be implanted along the same spinal cord level, or different spinal cord levels. The electrodes may be implanted in the patient's epidural space, or in proximity to one or more dorsal root ganglia, dorsal horn, dorsal column, or some combination thereof. Examples of electrical stimulation systems suitable for stimulating dorsal root ganglia are found in, for example, U.S. Patent Applications Publication Nos. 2013/0317583; 2013/0317585; 2013/0317586; 2013/0317587; and 2013/0317588, all of which are incorporated by reference.

In at least some embodiments, the neuronal activity desired to be disrupted is synchronous. In some embodiments, the electrical stimulation signals generated by the two or more electrodes (or sets of electrodes) create effective electric fields (e.g., electrical stimulation propagating from the electrodes sufficient to cause an excitatory effect on axons surrounding the electrodes) that function to reset the undesired neural activity in a coordinated manner.

In order to generate sufficient effective electric fields for disrupting the undesired neuronal activity, the two or more electrodes (or sets of electrodes) may employ the same stimulation parameters, or may have one or more different stimulation parameters. The size and shape of the effective electric fields generated by the two or more electrodes (or sets of electrodes) at a given set of stimulation parameters can be determined by observation of the effects of stimulation. Alternately (or additionally), the size and shape of the effective electric fields generated by the two or more electrodes (or sets of electrodes) at a given set of stimulation parameters can be determined, or stimulated, using one or more computer models (e.g., Volume of Tissue Activated Model, Stimulation Field Model, or the like or combinations thereof). As indicated above, the effective volume of an electric field is based on the region of tissue that experiences a stimulating effect in response to the electric field. Outside this effective volume, the electric field is too weak to stimulate the tissue. Information obtained from the computer models may facilitate selection of implantation locations, or facilitate selection of stimulation parameters, or both.

In some embodiments, the two or more electrodes (or sets of electrodes) generate effective electric fields that are temporally offset (e.g., time-delayed) from one another such that the effective electric fields are out of phase from one another. In at least some embodiments, the two or more electrodes (or sets of electrodes) are situated such the effective electric fields generated by the two or more electrodes (or sets of electrodes) stimulate different populations of neurons in communication with one another (e.g., different neurons along a particular neural pathway). Although not wishing to be bound by a particular theory, the offsetting of the effective electric fields generated by the two or more electrodes (or sets of electrodes) may be such that the downstream neurons are in a refractory period while the upstream neurons are propagating action potentials. In which case, the action potentials may be unable to propagate from the upstream neurons to the downstream neurons. Accordingly, undesired neuronal activity may be desynchronized and, therefore, disrupted.

Any suitable time delay may be implemented between the two or more electrodes (or sets of electrodes) for disrupting undesired neuronal activity. In some embodiments, the time delay may be determined by testing and observation. In some embodiments, the time delay is determined based on the frequency of the undesired neural activity (e.g., an observed shifted theta-band frequency) to be desynchronized. For example, in at least some embodiments N electrodes, where N is the number of different electrodes (or sets of electrodes) (or populations of neurons to be desynchronized) greater than or equal to 2, are driven such that there is a time delay of $1/(f \times N)$, where f is a frequency that is on or around the frequency of the undesired neural activity (e.g., an observed shifted theta-band frequency) to be desynchronized. In some embodiments, f is the same as the frequency as the undesired neuronal activity. In other embodiments, f is within 10 Hz, 9 Hz, 8 Hz, 7 Hz, 6 Hz, 5 Hz, 4 Hz, 3 Hz, 2 Hz, or 1 Hz above or below the frequency of the undesired neuronal activity.

When the generated effective electric fields are time-delayed from one another, it may be desirable for the effective electric fields to have little or no overlap in order to coordinate the resetting of the action potential propagation by stimulating different populations of cells that are in communication with one another. In at least some embodiments, the two or more electrodes (or sets of electrodes) are situated such that the nearest outer edges of the generated effective electric fields are at least 1 cm, 2 cm, 3 cm, 4 cm, or 5 cm apart from one another. In at least some embodiments, the two or more electrodes (or sets of electrodes) are situated such that the nearest outer edges of the generated effective electric fields are no more than 5 cm, 4 cm, 3 cm, 2 cm, or 1 cm apart from one another. In at least some embodiments, the two or more electrodes (or sets of electrodes) are situated such that there is little (no more than 20%, 10%, 5%, or less), if any, overlap in the effective volumes of the generated effective electric fields.

Alternately, the two or more electrodes (or sets of electrodes) are situated such that the effective electric fields generated by the two or more electrodes (or sets of electrodes) have substantial (at least 50%, 60%, 70%, 80%, 90%, 95%, or more of the effective volumes of the electric fields) overlap. When there is substantial overlap of effective electric fields between the two or more electrodes (or sets of electrodes), the stimulation parameters of the two or more electrodes (or sets of electrodes) may be varied from one another in order to preferentially target some neurons more than others.

It has been shown that some stimulation parameters may preferentially target some neurons more than others. At least some physical characteristics of neurons (e.g., axon diameters, the presence or absence of a myelin sheath, or the like) may affect whether or not those neurons are excited by an effective electric field having a particular set of stimulation parameters. Consequently, in at least some embodiments, the stimulation parameters of at least one of the generated effective electric fields is varied in response to one or more physical characteristics of the neurons along the overlapping portion of the generated effective electric fields (e.g., axon diameters, the presence or absence of a myelin sheath, or the like).

The different stimulation parameters may enable a first set of stimulation parameters of a first electrode to stimulate a first set of target neurons and a second set of stimulation parameters of a second electrode to stimulate a second set of target neurons. In some embodiments, the second set of target neurons is a subset of the first set of target neurons. In which case, one narrow example of a stimulation procedure may include only a portion of the overall population of neurons within an overlapping portion of the effective electric fields becoming excitable during stimulation by a first electrode (or set of electrodes) with a first set of stimulation parameters, while all (or nearly all) of the overall population of neurons within the overlapping portion of the effective electric fields becoming excitable during stimulation by a second electrode (or set of electrodes) with a second set of stimulation parameters.

In other embodiments, the second set of target neurons is mutually exclusive of the first set of target neurons. In which case, one narrow example of a stimulation procedure may include a first portion of the overall population of neurons within an overlapping portion of the effective electric fields becoming excitable during stimulation by a first electrode (or set of electrodes) with a first set of stimulation parameters, and a second portion (mutually exclusive of the first portion) of the overall population of neurons within the overlapping portion of the effective electric fields becoming excitable during stimulation by a second electrode (or set of electrodes) with a second set of stimulation parameters.

In at least some embodiments, stimulation can be timed between the two or more electrodes (or sets of electrodes) such that some neurons are in a refractory period while other neurons are propagating action potentials. In which case, at least some of the action potentials are unable to propagate along the entire length of the neuronal pathway. Accordingly, undesired neuronal activity may be disrupted through desynchronization.

Figure 7:
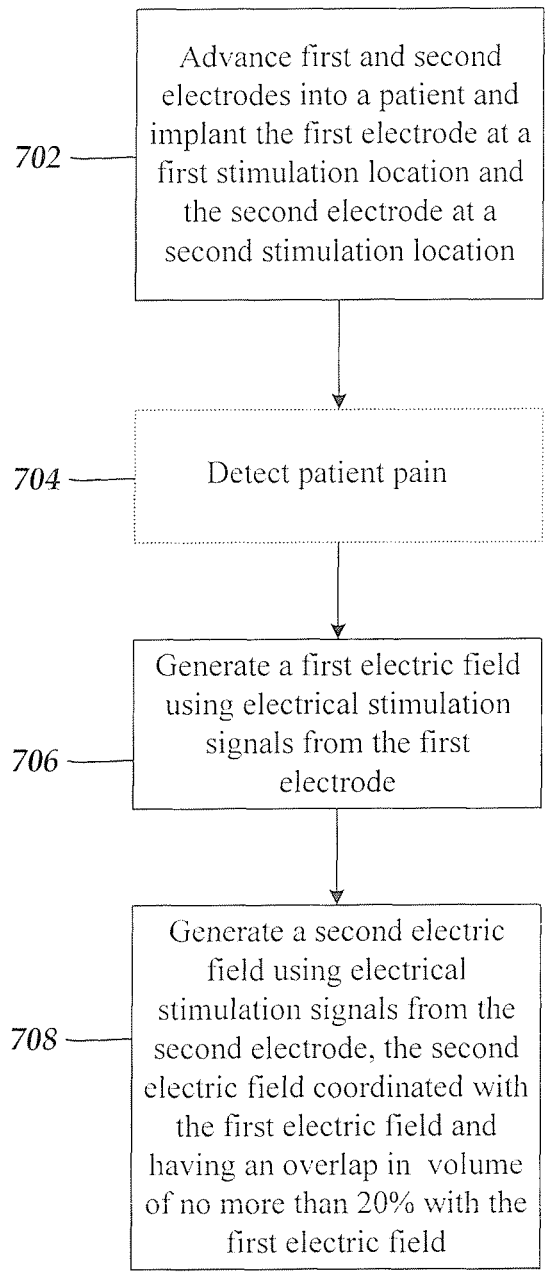
FIG. 7 is a flowchart of another embodiment of a technique for disrupting undesired neural activity through desynchronization of action potential propagation along patient tissue, according to the invention.
Figure 8:
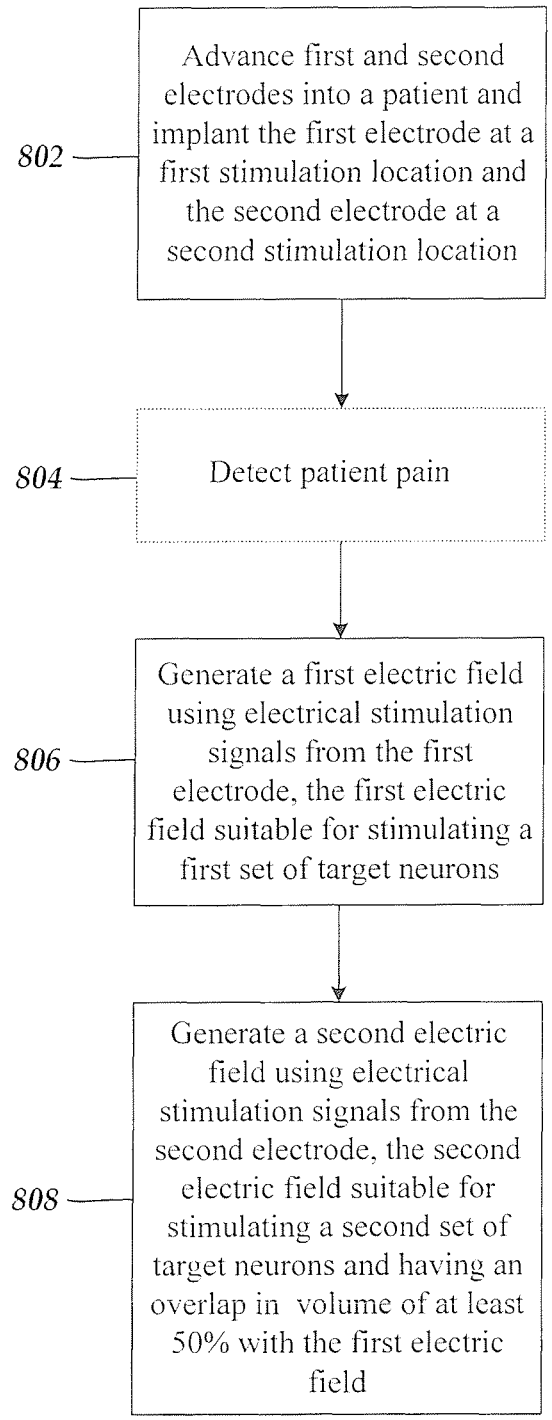
FIG. 8 is a flowchart of yet another embodiment of a technique for disrupting undesired neural activity through desynchronization of action potential propagation along patient tissue, according to the invention.

FIGS. 6-8 are flowcharts showing several different techniques for stimulating patient tissue to alleviate patient pain. FIG. 6 is a flowchart showing one embodiment of a stimulation procedure for disrupting undesired neural activity through desynchronization of action potential propagation along patient tissue. In step 602, first and second electrodes are advanced into a patient and implanted at first and second stimulation locations, respectively. A computer model may be used to facilitate the determination of the positioning of the first and second electrodes. Optionally, in step 604, patient pain is detected. The pain may be detected using any suitable technique including, for example, a pain measurement scale, patient feedback, a change in one or more monitored pain indicators (e.g., a frequency shift in the patient's theta wave activity), or the like. The pain indicator, such as a frequency shift, can be detected using any suitable monitoring technique (e.g., electroencephalography, or the like). The monitoring of the pain indicator can be performed using a sensor in communication with the control module. In step 606, a first effective electric field is generated using electrical stimulation signals from the first electrode. In step 608, a second effective electric field is generated using electrical stimulation signals from the second electrode, with the second effective electric field being time-delayed (e.g., out of phase) from the first effective electric field. The time-delay between the first and second effective electric fields may, optionally, be calculated based on a frequency of a detected undesired neural activity.

The generated second effective electric field may be partially overlapping (or non-overlapping) with the first effective electric field. The second effective electric field can have stimulation parameters that are either the same or different from stimulation parameters of the first effective electric field. A computer model may be used to adjust the stimulation parameters of first and second effective electric fields generated by the first and second electrodes, respectively. The computer model(s) can be used to adjust the location, the size, the shape (or any combination of the above) so that the generated effective electric fields are non-overlapping, or partially overlapping. Stimulation, via the first and second electrodes, may be initiated in response to the pain indicator, such as the detected frequency shift in the patient's theta band activity. The frequencies of the first and second effective electric fields can be based, at least in part, on the pain indicator, such as the frequency of the detected shift in theta band activity. The stimulation parameters of the first and/or second effective electric fields may be adjusted in response to a feedback loop, such as an observed frequency shift towards or away from a particular frequency or frequency range. The stimulation may be terminated in response to a feedback loop, such as an observed frequency shift towards or away from a particular frequency or frequency range.

FIG. 7 is a flowchart showing another embodiment of a stimulation procedure for disrupting undesired neural activity through desynchronization of action potential propagation along patient tissue. In step 702, first and second electrodes are advanced into a patient and implanted at first and second stimulation locations, respectively. A computer model may be used to facilitate the determination of the positioning of the first and second electrodes. Optionally, in step 704, patient pain is detected. The pain may be detected using any suitable technique including, for example, a pain measurement scale, patient feedback, a change in one or more monitored pain indicators (e.g., a frequency shift in the patient's theta wave activity), or the like. The pain indicator, such as a frequency shift, can be detected using any suitable monitoring technique (e.g., electroencephalography, or the like). The monitoring of the pain indicator can be performed using a sensor in communication with the control module. In step 706, a first effective electric field is generated using electrical stimulation signals from the first electrode. In step 708, a second effective electric field is generated using electrical stimulation signals from the second electrode, with the second effective electric field coordinated with the first effective electric field. The generated second effective electric field has an overlap in volume of no more than 20% with the first effective electric field.

A computer model may be used to adjust the stimulation parameters of first and second effective electric fields generated by the first and second electrodes, respectively. The computer model(s) can be used to adjust the location, the size, the shape (or any combination of the above) so that the generated effective electric fields are non-overlapping, or partially overlapping. Stimulation, via the first and second electrodes, may be initiated in response to the pain indicator, such as the detected frequency shift in the patient's theta band activity. The frequencies of the first and second effective electric fields can be based, at least in part, on the pain indicator, such as the frequency of the detected shift in theta band activity. The stimulation parameters of the first and/or second effective electric fields may be adjusted in response to a feedback loop, such as an observed frequency shift towards or away from a particular frequency or frequency range. The stimulation may be terminated in response to a feedback loop, such as an observed frequency shift towards or away from a particular frequency or frequency range.

FIG. 8 is a flowchart showing yet another embodiment of a stimulation procedure for disrupting undesired neural activity through desynchronization of action potential propagation along patient tissue. In step 802, first and second electrodes are advanced into a patient and implanted at first and second stimulation locations, respectively. A computer model may be used to facilitate the determination of the positioning of the first and second electrodes. Optionally, in step 804, patient pain is detected. The pain may be detected using any suitable technique including, for example, a pain measurement scale, patient feedback, a change in one or more monitored pain indicators (e.g., a frequency shift in the patient's theta wave activity), or the like. The pain indicator, such as a frequency shift, can be detected using any suitable monitoring technique (e.g., electroencephalography, or the like). The monitoring of the pain indicator can be performed using a sensor in communication with the control module. In step 806, a first effective electric field is generated using electrical stimulation signals from the first electrode. The first effective electric field is suitable for stimulating a first set of target neurons. In step 808, a second effective electric field is generated using electrical stimulation signals from the second electrode. The second effective electric field is suitable for stimulating a second set of target neurons. The second effective electric field has on overlap in volume of at least 50% with the first effective electric field. The second set of target neurons can be a subset of the first set of target neurons, or mutually exclusive of the first set of target neurons. The stimulation parameters of the first and second effective electric fields may be calculated based on one or more physical characteristics of at least some of the neurons in the overlapping portion of the first and second effective electric fields. The one or more physical characteristics may include, for example, axon diameters, the presence or absence of a myelin sheath, or the like.

A computer model may be used to adjust the stimulation parameters of first and second effective electric fields generated by the first and second electrodes, respectively. The computer model(s) can be used to adjust the location, the size, the shape (or any combination of the above) so that the generated effective electric fields are non-overlapping, or partially overlapping. Stimulation, via the first and second electrodes, may be initiated in response to the pain indicator, such as the detected frequency shift in the patient's theta band activity. The frequencies of the first and second effective electric fields can be based, at least in part, on the pain indicator, such as the frequency of the detected shift in theta band activity. The stimulation parameters of the first and/or second effective electric fields may be adjusted in response to a feedback loop, such as an observed frequency shift towards or away from a particular frequency or frequency range. The stimulation may be terminated in response to a feedback loop, such as an observed frequency shift towards or away from a particular frequency or frequency range.

It will be understood that the system can include one or more of the methods described hereinabove with respect to FIGS. 6-8 in any combination. The methods, systems, and units described herein may be embodied in many different forms and should not be construed as limited to the embodiments set forth herein. Accordingly, the methods, systems, and units described herein may take the form of an entirely hardware embodiment, an entirely software embodiment or an embodiment combining software and hardware aspects. The methods described herein can be performed using any type of processor or any combination of processors where each processor performs at least part of the process.

It will be understood that each block of the flowchart illustrations, and combinations of blocks in the flowchart illustrations and methods disclosed herein, can be implemented by computer program instructions. These program instructions may be provided to a processor to produce a machine, such that the instructions, which execute on the processor, create means for implementing the actions specified in the flowchart block or blocks or described for the control modules, external programming units, remote data storage units, systems and methods disclosed herein. The computer program instructions may be executed by a processor to cause a series of operational steps to be performed by the processor to produce a computer implemented process. The computer program instructions may also cause at least some of the operational steps to be performed in parallel. Moreover, some of the steps may also be performed across more than one processor, such as might arise in a multi-processor computer system. In addition, one or more processes may also be performed concurrently with other processes, or even in a different sequence than illustrated without departing from the scope or spirit of the invention.

The computer program instructions can be stored on any suitable computer-readable medium including, but not limited to, RAM, ROM, EEPROM, flash memory or other memory technology, CD-ROM, digital versatile disks ("DVD") or other optical storage, magnetic cassettes, magnetic tape, magnetic disk storage or other magnetic storage devices, or any other medium which can be used to store the desired information and which can be accessed by a computing device.

The above specification and examples provide a description of the manufacture and use of the invention. Since many embodiments of the invention can be made without departing from the spirit and scope of the invention, the invention also resides in the claims hereinafter appended.

What is claimed as new and desired to be protected by Letters Patent of the United States is:

1. An electrical stimulation system, comprising:
an implantable control module configured and arranged for implantation in a body of a patient and comprising a processor, wherein the control module is configured and arranged to provide electrical stimulation signals to a plurality of electrodes electrically-coupled to the control module and configured and arranged for electrical stimulation of patient tissue to treat patient pain;
a first electrode disposed on at least one electrical stimulation lead in a spinal cord of the patient, wherein the processor is configured and arranged to generate a first effective electric field suitable for stimulating patient tissue using the first electrode and the electrical stimulation signals provided from the control module;
a second electrode disposed on the at least one electrical stimulation lead in the spinal cord of the patient, wherein the processor is configured and arranged to generate a second effective electric field suitable for stimulating patient tissue using the second electrode and the electrical stimulation signals provided from the control module, wherein the processor is configured and arranged to generate the second effective electric field time-delayed from the first effective electric field such that the second effective electric field is out of phase with the first effective electric field; and
a sensor in communication with the processor, the sensor configured and arranged for monitoring patient theta-band activity and detecting frequency shifts, wherein the processor is configured and arranged to generate the first and second effective electric fields using the first and second electrodes in response to a shift in frequency of the theta-band activity detected by the sensor.

2. The electrical stimulation system of claim 1, wherein the processor is configured and arranged for determining the time delay between the first effective electric field and the second effective electric field based on the first detected shift in frequency of the theta-band activity.

3. The electrical stimulation system of claim 1, wherein the processor is configured and arranged to generate the first and second effective electric fields only when the shift in frequency of the theta-band activity is at least 0.5 Hz.

4. The electrical stimulation system of claim 1, wherein the processor is configured and arranged to adjust at least one of amplitude, frequency, impedance, voltage, or pulse width of the electrical stimulation signals provided to the first electrode and the second electrode in response to the sensor detecting another shift in frequency of the theta-band activity.

5. The electrical stimulation system of claim 1, wherein the processor is configured and arranged to terminate the electrical stimulation signals provided to the first electrode and the second electrode in response to the sensor detecting another in frequency of the theta-band activity.

6. The electrical stimulation system of claim 1, further comprising a computer model in communication with the processor, the computer model configured and arranged for coordinating with the processor to facilitate the positioning of the first electrode and the second electrode in the spinal cord of the patient.

7. The electrical stimulation system of claim 1, further comprising a computer model in communication with the processor, the computer model configured and arranged for coordinating with the processor to adjust at least one of amplitude, frequency, impedance, voltage, or pulse width of at least one of the first effective electric field or the second effective electric field.

8. The electrical stimulation system of claim 1, further comprising an actuator located external to the patient and in communication with the processor, the actuator configured and arranged for causing the control module to initiate providing the electrical stimulation signals to the at least one electrical stimulation lead.

9. The electrical stimulation system of claim 1, further comprising an actuator located external to the patient and in communication with the processor, the actuator configured and arranged for causing the control module to terminate providing the electrical stimulation signals to the at least one electrical stimulation lead.

10. An electrical stimulation system, comprising:
an implantable control module configured and arranged for implantation in a body of a patient and comprising a processor, wherein the control module is configured and arranged to provide electrical stimulation signals to at least one electrical stimulation lead coupled to the implantable control module for stimulation of patient tissue to treat patient pain;
a first electrode disposed on at least one electrical stimulation lead in a spinal cord of the patient, wherein the processor is configured and arranged to generate a first effective electric field suitable for stimulating patient tissue using the first electrode and the electrical stimulation signals provided from the control module;
a second electrode disposed on the at least one electrical stimulation lead in the spinal cord of the patient, wherein the processor is configured and arranged to generate a second effective electric field suitable for stimulating patient tissue using the second electrode and the electrical stimulation signals provided from the control module, wherein the processor is configured and arranged to generate the first and second effective electric fields using the first and second electrodes so that the second effective electric field has an overlap in volume of no more than 20% with the first effective electric field; and
a sensor in communication with the processor, the sensor configured and arranged for monitoring patient theta-band activity and detecting frequency shifts.

11. The electrical stimulation system of claim 10, wherein the processor is configured and arranged to generate the first and second effective electric fields using the first and second electrodes so that the second effective electric field does not overlap in volume with the first effective electric field.

12. The electrical stimulation system of claim 10, further comprising a computer model in communication with the processor, the computer model configured and arranged for coordinating with the processor to facilitate the positioning of the first electrode and the second electrode in the spinal cord of the patient such that the second effective electric field has an overlap in volume of no more than 20% with the first effective electric field.

13. The electrical stimulation system of claim 10, further comprising a computer model in communication with the processor, the computer model configured and arranged for coordinating with the processor to adjust at least one of amplitude, frequency, impedance, voltage, or pulse width of at least one of the first effective electric field or the second effective electric field such that the second effective electric field has an overlap in volume of no more than 20% with the first effective electric field.

14. An electrical stimulation system, comprising:
an implantable control module configured and arranged for implantation in a body of a patient and comprising a processor, wherein the control module is configured and arranged to provide electrical stimulation signals to at least one electrical stimulation lead coupled to the implantable control module for stimulation of patient tissue to treat patient pain;
a first electrode disposed on at least one electrical stimulation lead in a spinal cord of the patient, wherein the processor is configured and arranged to generate a first effective electric field suitable for stimulating a first set of target neurons within patient tissue using the first electrode and the electrical stimulation signals provided from the control module;
a second electrode disposed on the at least one electrical stimulation lead in the spinal cord of the patient, wherein the processor is configured and arranged to generate a second effective electric field suitable for stimulating a second set of target neurons that is different from the first set of target neurons within patient tissue using the second electrode and the electrical stimulation signals provided from the control module, wherein the processor is configured and arranged to generate the first and second effective electric fields using the first and second electrodes so that the second effective electric field has an overlap in volume of at least 50% with the first effective electric field; and
a sensor in communication with the processor, the sensor configured and arranged for monitoring patient theta-band activity and detecting frequency shifts.

15. The electrical stimulation system of claim 14, wherein the second set of target neurons is a subset of the first set of target neurons.

16. The electrical stimulation system of claim 14, wherein the second set of target neurons is mutually exclusive of the first set of target neurons.

* * * * *